United States Patent [19]

Kirby et al.

[11] Patent Number: 5,783,692
[45] Date of Patent: Jul. 21, 1998

[54] ALKYL POLYSACCHARIDE DERIVATIVES AND COMPOSITIONS

[75] Inventors: Andrew Francis Kirby, Footscray; Keith Moody, Watsonia North, both of Australia

[73] Assignee: ICI Australia Operations Proprietary Limited, Melbourne, Australia

[21] Appl. No.: 849,947

[22] PCT Filed: Dec. 22, 1995

[86] PCT No.: PCT/AU95/00871

§ 371 Date: Aug. 21, 1997

§ 102(e) Date: Aug. 21, 1997

[87] PCT Pub. No.: WO96/20203

PCT Pub. Date: Jul. 4, 1996

[30] Foreign Application Priority Data

Dec. 23, 1994 [AU] Australia ................... PN0299

[51] Int. Cl.$^6$ .............. C07H 13/04; C07H 1/00; A61K 31/715; A01N 25/00

[52] U.S. Cl. ............. 536/123.1; 424/405; 424/DIG. 8; 514/25; 514/54; 536/120

[58] Field of Search ............. 514/25, 54; 424/405, 424/DIG. 8; 536/120, 123.1

[56] References Cited

U.S. PATENT DOCUMENTS 5,580,553  12/1996  Nakajima .

FOREIGN PATENT DOCUMENTS

| 48667/79 | 4/1982 | Australia . |
| 454 321 A2 | 10/1991 | European Pat. Off. . |
| 1541055 | 3/1979 | United Kingdom . |

*Primary Examiner*—John Kight
*Assistant Examiner*—Howard C. Lee
*Attorney, Agent, or Firm*—Pillsbury Madison & Sutro LLP

[57] ABSTRACT

This invention relates to novel alkylpolysaccharide dertivatives including their salts and compositions comprising said alkyl polysaccharides. The alkyl polysaccharide derivatives are of the formula (I): $R^1—(OG)_n(X)_m$, where $R^1$ is hydrogen or a hydrophobic moiety; G is a saccahride residue; and X is a succinic anhydride residue; and n and m are independently chosen from an average value which is between 1 and 200.

28 Claims, No Drawings

ALKYL POLYSACCHARIDE DERIVATIVES AND COMPOSITIONS

This invention relates to novel alkyl polysaccharide derivatives and compositions comprising said alkyl polysaccharide derivatives and their salts. The alkylpolysaccharide derivatives of the current invention are particularly useful as surfactants and or adjuvants in compositions for use in agrochemical, animal health, personal care industries and the like.

Surfactants and compositions comprising surfactants are well known in general as components of industrial cleaners, agrochemical compositions such as herbicides, acaricides and pesticides and many types of personal care products such as shampoos, hair conditioners and the like.

Many surfactants can be used to form concentrates of active agents which concentrates may be readily emulsifiable into water. The ability of surfactants to emulsify lipophilic components to form aqueous compositions makes them particularly useful.

Many different compounds have been shown to have properties which makes them suitable for use as a surfactant. For example, it is well known in the art to use many surfactants such as alkyl phenol alkoxylates and fatty alcohol alkoxylates (also known as fatty alcohol polyalkyleneglycol ethers) and sulphate and phosphate esters thereof; vegetable oil alkoxylates (such as castor oil alkoxylates); alkyl and alkylaryl sulphonates; alcohol sulphates; sulphosuccinate mono-esters and di-esters; alkylene oxide block copolymers; and end carboxylated alkoxylates (ether carboxylates). Mixed alkoxylate surfactants may also be used, such as in the ethoxylate/propoxylate based surfactants. In recent years personal care products have primarily included surfactants comprising fatty acid glycolic esters, glycol stearates, glycerol stearates, ether sulphates, betaines, alkanolamides, amines and derivatives thereof.

Many of the surfactants of the prior art are not suitable for use in personal care products because they are potential skin sensitisers or irritants. Many factors influence the irritation effect of surfactants and the molecular structure of the surfactant can be closely linked to its effect on adsorption, solubilisation, penetration, swelling, denaturation and general irritation on human skin.

Because of their effect on the living systems in our environment, some surfactants are no longer acceptable for industrial use. Some surfactants of the prior art include toxic trace impurities such as nitrosamines which may have a detrimental effect on plant or human tissue which contact the surfactant. Other surfactants have had their use restricted because of their poor biodegradation properties and potential unfavourable effect on the environment.

In very recent times alkylpolysaccharides have become particularly attractive for use as surfactants because they contain no toxic trace impurities, they are readily biodegradable and because they are derived from renewable resources such as coconut oil and wheat starch. They are particularly favoured for use in personal care products because they demonstrate very little tendency to skin irritation.

It has now been found that novel environmentally acceptable alkyl polysaccharide derivatives can be produced having characteristics which make them particularly suited to use in agrochemical formulations (including animal health products such as drenches, pour-ons and dips), personal care products, fabric softeners and like consumer products.

The current invention therefore provides alkyl polysaccharide derivatives formed by the reaction of succinic anhydrides and alkylpolysaccharides.

The alkyl polysaccharide derivatives of the invention contain a carboxylic acid group which readily forms salts and hence the alkyl polysaccharide derivatives of the invention include the carboxylate salts thereof.

In the context of the present invention and patent specification the term alkenyl succinic anhydride is used to mean the reaction product of an olefin and maleic anhydride. Therefore, it will be evident to those skilled in the art that such reaction products may contain one or more compounds depending on whether the olefin is a pure olefin or, as is commonly found with industrial grades of olefins, a range of olefins. Usually such mixed olefins are identified by their average carbon chain length. For example, a $C_{12}$ olefin may contain olefins ranging from $C_8$ to $C_{16}$ but will have an average $C_{12}$ chain length and comprise predominantly the $C_{12}$ chain length olefin. One of the preferred olefins used for the manufacture of surfactants are the alpha-olefins.

It will be known to the skilled person that alkenyl succinic anhydrides may be produced by reacting maleic anhydride preferably with a 50 to 200% excess of an alpha-olefin at a temperature in the range of 150° to 400° C. and preferably 180° to 250° C. and removing excess alpha-olefin for example by vacuum distillation. No catalyst is generally necessary, but it is preferred that an antioxidant be present. These anhydrides are well known commercial materials. In alkenyl succinic anhydrides prepared as described above the double bond normally lies in the 2-position in the alkenyl substituent. However, other alkenyl isomers may be formed and hence these anhydrides may comprise mixtures of isomers.

In the context of the present invention and patent specification the term alkyl polysaccharide (or alkyl polyglycoside) is used to mean the reaction product of a saccharide residue and one or more alcohols, (strictly speaking the products of such a reaction should be called alkyl oligosaccharides, however, the more popular term alkyl polysaccharide is used herein as discussed in Ullman's "Encyclopedia of Industrial Chemistry" published by VCH. The average number of saccharide residues per molecule is usually between 1 and 3 and depending on the reaction parameters, the average number of saccharide residues can be greater than 3.

It will be evident to the skilled person that the alkyl polysaccharides used in the preparation of the novel alkyl polysaccharide derivatives of the present invention will comprise mixtures. First the reaction product may contain one or more compounds depending on whether the alcohol used in the preparation of the alkyl polysaccharide is a pure alcohol, or, as is commonly found with industrial grades of alcohols, a range of alcohols identified by their average carbon chain length. Second the alkyl polysaccharide may contain one or more saccharide residues. Third, if more than one saccharide residue is present the polysaccharide linkage may vary, for example in the case of glucose may be 1, 4 or more commonly 1,6 or a mixture thereof. Fourth, the anomeric centre in a saccharide ring may be in the alpha or beta position. Hence, in the context of the present invention and the patent specification the term alkyl polysaccharide is used to include each of these isomers and homologues and mixtures thereof.

In preparing the alkyl polysaccharide derivative of the present invention, a mixture of isomers may be formed as a result of the anhydride ring opening by nucleophilic attack on the anhydride carbonyl either close to or remote from the alkenyl groups. Moreover, reaction may occur at one or more of the primary or secondary alcohol groups of the alkyl polysaccharide.

From the above it will be evident to those skilled in the art, that as the alkenylsuccinic anhydride and the alkyl polysaccharide may each comprise one compound or a mixture of compounds and the reaction preparing the alkyl polysaccharide derivatives of the present invention may result in the formation of isomers or mixtures thereof, the alkyl polysaccharide derivatives of the present invention may comprise a single isomer or a mixture of isomers and homologues. Thus it should be understood that any structure or name used in this specification to define the alkyl polysaccharide derivatives of the present invention is meant to be representative of the possible isomers and homologues and not to be limiting to the specific name(s) or structures(s) represented.

Accordingly, in a further aspect the current invention provides alkyl polysaccharide derivatives of the general formula I.

where
R$^1$ is hydrogen or a hydrophobic moiety;
G is a saccharide residue, and
X is a succinic anhydride residue,
and n and m are independently chosen from an average value which is between 1 and 200.

The group R$^1$ may be an optionally substituted hydrocarbon group. More specifically, the group R$^1$ can be an alkyl, cycloalkyl, aryl, alkaryl, aralkyl or alkenyl group and is more preferably an alkyl group.

In a preferred embodiment R$^1$ is chosen from C$_1$ to C$_{40}$ branched or linear alkyl groups. More preferably R$^1$ is chosen from the group comprising C$_1$ to C$_{14}$ branched or linear alkyl groups and may even more preferably be chosen from C$_4$ to C$_{12}$ linear alkyl.

The saccharide residue G may be derived from one or more fructose, glucose, aldose, altose, idose, arabinose, xylose, lysose and ribose or from mixtures thereof. The group G is conveniently derived from glucose units and the glycoside is then a glucoside. If derived from sucrose the groups will comprise fructose and glucose residues.

The succinic anhydride residue preferably comprises an alkenyl or alkyl chain chosen from the group comprising C$_1$ to C$_{40}$ linear or branched alkenyl or alkyl groups or more preferably C$_6$ to C$_{30}$ linear alkenyl or alkyl chains or even more preferably C$_8$ to C$_{30}$ linear alkenyl or alkyl chains. In a particularly preferred embodiment the succinic anhydride comprises an alkenyl or alkyl chain of C$_8$, C$_{10}$, C$_{12}$, C$_{14}$, C$_{16}$ or C$_{18}$.

The alkylpolysaccharide derivatives of the invention in which the succinic anhydride residue comprises an alkyl chain may be prepared from the corresponding alkyl succinic anhydride and alkyl polysaccharide. The alkylsuccinic anhydride may be prepared from the corresponding alkenylsuccinic anhydride by hydrogenation. Typically, hydrogenation of the anhydride is carried out over a hydrogenation catalyst such as Raney nickel or a Pd/C catalyst. Temperatures of from 15° to 100° C. and pressures up to 200 bar absolute may be used and, if desired a solvent may be present. For example, the hydrogenation of an alkenylsuccinic anhydride may be carried out at 20° C. at 1 bar H$_2$ pressure using 5% w/w Pd/C catalyst over a period of, for example 6, to 24 hours.

Alternatively the alkylpolysaccharide derivatives of the invention in which the succinic anhydride residue comprises an alkyl chain may be prepared from the corresponding compounds of the invention in which the succinic anhydride residue comprises an alkenyl chain by hydrogenation.

In a particularly preferred embodiment the degree of glucosidation (dG), that is the number of saccharide (glucose) residues (n), is between 1 and 3.0. It is typically 1.1, preferably at least 1.2 and especially at least 1.3. The value of n is typically not greater than 5, and preferably not greater than 4, for example not greater than 2.

The actual mole ratio of succinic anhydride to alkyl polysaccharide used will vary according to the product(s) required from the reaction. Conveniently the mole ratio of the succinic anhydride to alkylpolysaccharide will be 1:1 but higher mole ratios may be used to prepare alkylpolysaccharide derivatives of the invention comprising more than one succinic anhydride residue or mixtures comprising an average of more than one succinic anhydride residue.

For example, one of the products of the reaction of the current invention between an alkyl polysaccharide and alkenyl succinic anhydride may be the product of formula II;

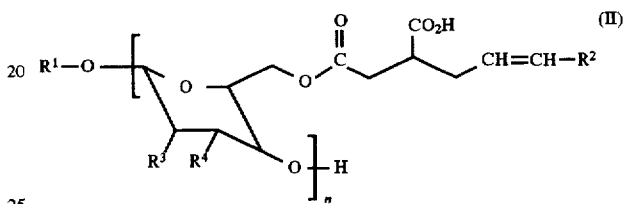

where
R$^1$ and R$^2$ are independently is hydrogen or C$_1$ to C$_{40}$ branched or linear alkyl groups,
R$^3$ and R$^4$ are independently chosen from the group comprising hydrogen, hydroxy, alkyl or alkoxy groups, and n is 1 to 100.

Preferably the product of formula II comprises R$^1$ chosen from the group comprising C$_1$ to C$_{12}$ branched or linear alkyl groups. R$^2$ is chosen from the group comprising C$_3$ to C$_{27}$ linear alkyl groups, R$^3$ and R$^4$ are hydroxy and n is between 1 and 2.5.

Another of the products of the reaction of the current invention between an alkyl polysaccharide and alkenyl succinic anhydride may be the product of formula III;

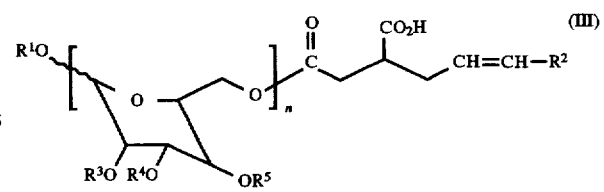

where
R$^1$ is a C$_1$ to C$_{12}$ branched or linear alkyl group,
R$^2$ is a C$_3$ to C$_{27}$ branched or linear alkyl group,
and R$^3$, R$^4$ and R$^5$ are independently chosen from the group comprising hydrogen, alkyl and acyl groups.

As indicated above, any structure or name used in this specification to define the alkylpolysaccharide derivatives of the present invention is meant to be representative of the possible isomers and homologues and not to be limiting to the specific name(s) or structures(s) represented. Although not wishing to be bound to the specific structure one of the preferred alkylpolysaccharide derivatives of the invention is believed to be of formula III.

The current invention also provides a method of preparation of alkyl polysaccharide derivatives of formula I, by reaction of a succinic anhydride with an alkyl polysaccharide.

Depending on the precise alkylpolysaccharide and alkenylsuccinic anhydride used, it is commonly possible that the reaction may be carried out in the absence of solvent. The temperature of reaction would in most cases be governed by the melting point of the alkylpolysaccharide which in general means that the optimal reaction temperature is above 120° C. and typically in the range of 130° to 160° C. Generally at these temperatures and in the absence of significant stirring the unreacted alkylpolysaccharide and alkenylsuccinic anhydride form two separate phases, the upper phase comprising the alkenylsuccinic anhydride. On vigorous mixing, the alkylpolysaccharide and alkenylsuccinic anhydride react to quickly form a single phase. Typically heating may be applied for 2 to 4 hours to ensure that reaction is complete. Progress of the reaction can be followed by any convenient spectroscopic technique such as infra-red spectroscopy.

It is within the scope of the method for the preparation of the alkylpolysaccharide derivatives of formula I to react the reaction product from the preparation of an alkylpolysaccharide with a succinic anhydride. In general alkylpolysaccharides are prepared by reaction of an excess of alcohol with a saccharide and hence the reaction product contains an alcohol and the alkylpolysaccharide. Therefore, the reaction product of such an alcohol/alkylpolysaccharide mixture and a succinic anhydride may comprise a mixture of the alkylpolysaccharide derivative of formula I and esters formed from the alcohol and the succinic anhydride. Such mixed reaction products may in their own right be useful as surfactants and/or adjuvants.

It will be evident to those skilled in the art that the alkylpolysaccharides used in the preparation of the alkylpolysaccharide derivatives of the invention may be prepared according to a number of processes well known in the art including the process taught in European Patent No. 0132043.

In general the products of the reaction between alkylpolysaccharide and alkenyl succinic anhydride will be soluble in relatively non-polar solvents, such as aromatics including toluene, xylene and the range of SOLVESSO aromatic solvents such as SOLVESSO 150. (SOLVESSO is a trade mark of Esso (Exxon) Chemicals Limited.) In general the products of the reaction are sparingly soluble in water but the solubility in aqueous media can be increased by forming a corresponding salt. Hence the alkylpolysaccharide derivatives of the invention includes the alkali and alkaline earth metal and amine salts thereof. For example many of the products of the reaction of the current invention will be capable of forming a triethanolamine salt through the free carboxyl group.

It will be readily apparent to the person skilled in the art that the alkylpolysaccharide derivatives of the current invention are suitable for use in many different types of formulations including micro-emulsions, macro-emulsions, emulsifiable concentrates, solutions, colloids, suspensions, powders, granules and the like.

The alkyl polysaccharide derivatives of the current invention are suitable for use as surfactants in many agrochemical formulations including pesticides such as insecticides, fungicides, herbicides and animal health products such as drenches, pour-ons and dips. The alkyl polysaccharide derivatives of the current invention are suitable for use in other types of formulations including personal care products and fabric conditioners and defoamers: the alkyl polysaccharide derivatives of the current invention are also useful as emulsifiers for wax, silicone and polymer emulsions used in, for example, polishes and textile treatment formulations, as emulsifiers for solvents used in industrial and institutional cleaning formulations, where they have benefits as fugitive surfactants, that is surfactants which complete their action and are then readily degraded with loss of surfactancy, and as emulsifiers in emulsion polymerisation of a wide variety of monomers.

In particular, the current invention further provides formulations comprising the alkylpolysaccharide (APS) derivatives of the current invention and an active pesticidal component. The formulations may be useful as a pesticide, fungicide, bactericide, insecticide, insect antifeedants, acaricides, miticide, nematocide, herbicide or plant growth regulator compositions or the like. The formulation may optionally comprise solvents and further surfactants and may be in the form of a solution, macroemulsion or microemulsion. Furthermore the formulation may comprise high active loading or low active loading.

The APS derivatives of the invention may have particular application in enhancing the efficacy of active ingredients including pesticides, fungicides, bactericides, insecticides, insect antifeedants, acaricides, miticides, nematocides, herbicides, plant growth regulators and the like. In such applications the APS derivatives of the invention may be referred to as adjuvants.

In one preferred embodiment the APS derivatives may be used as adjuvants and/or surfactants in the formulation of herbicides including phenoxypropionates, glyphosate (salts), triketones, alkylketones, sulphonylureas, sulphonanilides, and the like.

In another preferred embodiment, the APS derivatives of the current invention may be used in insecticide compositions having an active insecticide component chosen from the group comprising carbamates, organophosphates such as chlorpyriphos C.A. [2921-88-2] and phosmet C.A. [732-11-6] natural pyrethroids and synthetic pyrethroids such as cyhalothrin, permethrin Chemical Abstracts Registry no. [52645-53-1], cypermethrin C.A. [52315-07-8], alpha-cypermethrin, sumethrin, allethrin and mixtures thereof.

In a further preferred embodiment, the active herbicidal component may be chosen from the group comprising hormone esters such as esters of 2,4-dichlorophenoxyacetic acid (commonly known as 2,4-D) C.A.[94-75-7], or phenoxypropionates sold commercially under the trade names FUSILADE (fluazifop-p-butyl) and HOEGRASS (also known as diclofop-p-methyl). (FUSILADE and HOEGRASS are trade marks.)

Suitable solvents for use in the compositions of the current invention may be any one or more liquids capable of dissolving or miscible with the active compound of the pesticide formulation. Suitable solvents include alkyl aromatic solvents such as xylene, or the SOLVESSO series of solvents, particularly SOLVESSO 100, SOLVESSO 150 and SOLVESSO 200.

In addition to the APS derivatives, the compositions of the current invention, may comprise secondary surfactants which may comprise any one or more surface active agents known in the art. Suitable surfactants include non-ionic surface active agents which are chemically inert and do not ionise in aqueous solutions. Preferably they do not form salts with metallic ions and exhibit good solution stability in hard or saline waters and in the presence of reasonable concentrations of acids and bases. The TERIC series of surfactants such as the TERIC N-series and TERIC 200 including TERIC N15 and TERIC GN8 are particularly preferred. (TERIC is a registered trade mark of ICI Australia Operations Proprietary Limited).

The current invention will now be further described with reference to the following non-limiting examples;

EXAMPLE 1

A $C_{12}$ alpha-olefin was added to an equimolar quantity of maleic acid and heated to 220° C. to form an alkenyl succinic anhydride. An equimolar quantity of a $C_4$ alkyl polysaccharide was added to the alkenyl succinic anhydride in the absence of any solvent and the mixture heated to 140° C. to form a $C_4$ alkyl polysaccharide product.

The $C_4$ polysaccharide product was readily soluble in SOLVESSO 150 at a concentration of 40 to 50% w/w.

EXAMPLE 2 n-Butylglucoside (dG 1.77; M 361.2)(72.2 g; 0.2 moles) was melted and added to a $C_{12}$ alkenyl succinic anhydride (M 266.4)(53.3 g; 0.2 moles) in the absence of any solvent and the mixture heated to 140° C. and stirred for 3 hours to form a $C_4$ polysaccharide product. The $C_4$ polysaccharide product was insoluble in water but readily soluble in SOLVESSO 150.

EXAMPLES 3 n-Butylglucoside (dG 1.77; M 361.2)(72.2 g; 0.2 moles) was melted and added to a $C_{14}$ alkenyl succinic anhydride (M 297.4)(59.5 g; 0.2 moles) in the absence of any solvent and the mixture heated to 140° C. with stirring. Initially the reactants formed two phases which emulsified on vigorous stirring. After 3.5 hours the reaction to form the $C_4$ polysaccharide product was complete. The $C_4$ polysaccharide product was insoluble in water but readily soluble in SOLVESSO 150.

EXAMPLE 4 n-Butylglucoside (dG 1.77; M 361.2)(54.2 g; 0.15 moles) was melted and added to a $C_{16}$ alkenyl succinic anhydride (M 326.1)(48.9 g; 0.15 moles) in the absence of any solvent and the mixture heated to 140° C. with stirring. Initially the reactants formed two phases which emulsified slowly with vigorous stirring. After several hours reaction formation of the $C_4$-alkyl polysaccharide product was complete. The $C_4$-alkyl polysaccharide product was insoluble in water but readily soluble in SOLVESSO 150.

EXAMPLE 5 n-Butylglucoside (dG 1.77; M 361.2)(54.2 g; 0.15 moles) was melted and added to a $C_{18}$ alkenyl succinic anhydride (M 348.2)(52.2 g; 0.15 moles) in the absence of any solvent and the mixture heated to 140° C. with stirring. Initially the reactants formed two phases which emulsified slowly with vigorous stirring. After 5 hours formation of the $C_4$-alkyl polysaccharide product was complete. The $C_4$-alkyl polysaccharide product was insoluble in water but readily soluble in SOLVESSO 150.

EXAMPLE 6

ECOTERIC AS20 (dG 1.50; M 401.6)(40.1 g; 0.1 moles), a $C_{10}$-alkyl polysaccharide of formula was melted and added to a $C_{14}$ alkenyl succinic anhydride (M 290.8)(43.6 g; 0.15 moles) in the absence of any solvent and the mixture kept at 140° C. with stirring. After one hour of commencing the reaction there was a significant increase in the viscosity of the reaction mixture. Samples were periodically removed from the reaction mixture and examined using infra-red spectroscopy in order to determine whether reaction was complete. Heating and stirring was continued for a further 5 hours until reaction was complete. A $C_{10}$-alkyl polysaccharide product was formed.

The $C_{10}$-alkyl polysaccharide product was readily soluble in hot SOLVESSO 150. (ECOTERIC is a trade mark of ICI Australia Operations Proprietary Limited.)

EXAMPLE 7

ECOTERIC AS20 (dG 1.50; M 401.6)(40.1 g; 0.1 moles) was melted and added to a C12 alkenyl succinic anhydride (M 266.4)(26.6 g; 0.1 moles) in the absence of any solvent and the mixture kept at 140° C. with stirring. Initially the reactants formed two phases but after a few minutes of heating and stirring a homogeneous molten mixture formed. Samples were periodically removed from the reaction mixture and examined using infra-red spectroscopy in order to determine whether reaction was complete. Heating and stirring was continued for a further 2 hours until the reaction to form the $C_{10}$-alkyl polysaccharide product was complete. The $C_{10}$-alkyl polysaccharide product was insoluble in water but soluble in ethanol and a solution of triethanolamine in water.

EXAMPLE 8

ECOTERIC AS20 (dG 1.50; M 401.6)(60.2 g; 0.15 moles) was melted and added to a C14 alkenyl succinic anhydride (M 290.8)(43.6 g; 0.15 moles) in the absence of any solvent and the mixture kept at 140° C. with stirring. Initially the reactants formed two phases but after a few minutes of heating and stirring a homogeneous, viscous molten mixture formed. Heating and stirring was continued for a further 2.5 hours until reaction to form the $C_{10}$-alkyl polysaccharide was complete.

EXAMPLE 9

ECOTERIC AS20 (dG 1.50; M 401.6)(60.2 g; 0.15 moles) was melted and added to a $C_{16}$ alkenyl succinic anhydride (M 326.1)(48.9 g; 0.15 moles) in the absence of any solvent and the mixture kept at 140° C. with stirring. Initially the reactants formed two phases but after a few minutes of heating and stirring a homogeneous, viscous molten mixture formed. Heating and stirring was continued for a further 2.5 hours until reaction to form the $C_{10}$-alkyl polysaccharide product was complete.

EXAMPLE 10

ECOTERIC AS20 (dG 1.50; M 401.6)(60.2 g; 0.15 moles) was melted and added to a $C_{18}$ alkenyl succinic anhydride (M 348.2)(52.2 g; 0.15 moles) in the absence of any solvent and the mixture kept at 140° C. with stirring. Initially the reactants formed two phases but after a few minutes of heating and stirring a homogeneous, viscous molten mixture formed. Heating and stirring was continued for a further 4 hours until reaction to form a $C_{10}$-alkyl polysaccharide product was complete.

EXAMPLE 11

ECOTERIC AS20 (dG 1.50; M 401.6)(40.1 g; 0.1 moles) was melted and added to a $C_{30}$ alkenyl succinic anhydride (M 517.0)(51.7 g; 0.1 moles) in the absence of any solvent and the mixture kept at 140° C. with stirring. Initially the reactants formed two phases but after a few minutes of heating and stirring a homogeneous, viscous molten mixture formed. Heating and stirring was continued for a further 4 hours until reaction was complete. The product was soluble in SOLVESSO 150.

EXAMPLE 12 n-Butylglucoside (dG 1.77, M 361.2)(72.2 g, 0.2 moles) and n-decenylsuccinic anhydride (average M 239.5)(47.9 g, 0.2 moles) were heated using an oil bath at 150° C. for 4.5 hours. The n-butylglucoside and n-decenylsuccinic anhydride were initially present as two separate phases but formed a single phase during reaction. The alkyl polysaccharide product was soluble in SOLVESSO 150.

EXAMPLE 13 n-Butylglucoside (dG 1.77, M 361.2)(72.2 g, 0.2 moles) and n-octenylsuccinic anhydride (average M 211.3)(42.3 g, 0.2 moles) were heated using an oil bath at 150° C. for 5 hours. The alkyl polysaccharide product was soluble in hot SOLVESSO 150.

EXAMPLE 14

ECOTERIC AS20 (n-decylglucoside) (dG 1.50, average M 401.6)(40.1 g, 0.1 moles) and n-octenylsuccinic anhydride (average M 211.3)(21.1 g, 0.1 moles) were heated using an oil bath at 140° C. for 4 hours. The alkyl polysaccharide product formed a 50% w/w solution in SOLVESSO 150.

EXAMPLE 15 n-Hexylglucoside (dG 1.78, average M 390.9)(78.2 g, 0.2 moles) and n-decenylsuccinic anhydride (average M 239.5) (47.9 g, 0.2 moles) were heated using an oil bath at 140° C. for 3 hours. The alkyl polysaccharide product formed was soluble in SOLVESSO 150.

EXAMPLE 16 n-Hexylglucoside (dG 1.78, average M 390.9)(78.2 g, 0.2 moles) and n-dodecenylsuccinic anhydride (53.3 g, 0.2 moles) were heated using an oil bath at 140° C. for 3 hours. The alkyl polysaccharide product formed was soluble in SOLVESSO 150.

EXAMPLE 17 n-Hexylglucoside (dG 2.39, M 489.8)(49.0 g, 0.1 moles) and n-dodecenylsuccinic anhydride (27.4 g, 0.1 moles) were heated using an oil bath at 150° C. for 5 hours. The n-hexylglucoside and n-dodecenylsuccinic anhydride were initially present as two separate phases which formed a single phase very quickly on mixing as reaction occurred to give the alkyl polysaccharide product.

EXAMPLE 18 n-Hexylglucoside (dG 1.32, M 316.3)(31.6 g, 0.1 moles) and n-dodecenylsuccinic anhydride (27.4 g, 0.1 moles) were heated using an oil bath at 150° C. for 2 hours to form the alkyl polysaccharide product.

EXAMPLE 19 n-Octylglucoside (dG 1.94, M 444.9)(89.0 g, 0.2 moles) and n-decenylsuccinic anhydride (47.9 g, 0.2 moles) were heated using an oil bath at 150° to 155° C. The n-octylglucoside and n-decenylsuccinic anhydride were initially present as two separate phases which formed a single phase very quickly on mixing as reaction occurred to give the alkyl polysaccharide product. Heating was continued for 2 hours. The alkyl polysaccharide product was soluble in SOLVESSO 150.

EXAMPLE 20 n-Octylglucoside (dG 1.94, M 444.9)(89.0 g, 0.2 moles) and n-octenylsuccinic anhydride (42.3 g, 0.2 moles) were heated using an oil bath at 145° to 155° C. for 3.5 hours to form an alkyl polysaccharide product.

EXAMPLE 21 n-Octylglucoside (dG 1.94, M 444.9)(89.0 g, 0.2 moles) and n-dodecenylsuccinic anhydride (53.3 g, 0.2 moles) were heated using an oil bath at 145° to 155° C. for 3.5 hours to form an alkyl polysaccharide product.

EXAMPLE 22

2-Ethylhexylglucoside (dG 2.16, average M 480.6) (96.1 g, 0.2 moles) and n-dodecenylsuccinic anhydride (53.3 g, 0.2 moles) were heated using an oil bath at 145° to 150° C. The ethylhexylglucoside and n-dodecenylsuccinic anhydride were initially present as two separate phases which formed a single phase on mixing as reaction progressed. Heating was continued for 6 hours until reaction was complete.

EXAMPLE 23

2-Ethylhexylglucoside (dG 2.16, average M 480.6)(96.1 g, 0.2 moles) and n-decenylsuccinic anhydride (47.9 g, 0.2 moles) were heated using an oil bath at 145° to 150° C. for 6 hours to form the alkyl polysaccharide product.

EXAMPLE 24

2-Ethylhexylglucoside (dG 2.16, average M 480.6)(96.1 g, 0.2 moles) and n-octenylsuccinic anhydride (42.3 g, 0.2 moles) were heated using an oil bath at 150° C. for 3 hours to form the alkyl polysaccharide product.

EXAMPLE 25

A mixed n-octylglucoside/n-decylglucoside (dG 1.92, average M 456.9) was synthesised by acid catalysed condensation of glucose with ALFOL 810D (a mixture of n-octanol and n-decanol)(average M 145.5). The mixed n-octylglucoside/n-decylglucoside (91.4 g, 0.2 moles) was heated at 150° to 155° C. with n-octenylsuccinic anhydride (42.3 g, 0.2 moles). Initially a layer of mixed n-octylglucoside/n-decylglucoside and a separate layer of n-octenylsuccinic anhydride were present but a single phase was readily formed on mixing as reaction occurred to give the product. Heating was continued for a further 2 hours until the reaction was complete.

EXAMPLE 26

A mixed n-octylglucoside/n-decylglucoside (dG 1.92, average M 456.9) was synthesised by acid catalysed condensation of glucose with ALFOL 810D (a mixture of n-octanol and n-decanol)(average M 145.5). The mixed n-octylglucoside/n-decylglucoside (91.4 g, 0.2 moles) was heated at 150° to 155° C. with n-decenylsuccinic anhydride (47.9 g, 0.2 moles). Heating was continued for a further 3 hours until the reaction was complete.

EXAMPLE 27

| Component | Proportion (g/dm$^3$) |
| --- | --- |
| lambda-cyhalothrin 91% w/w, Technical Grade | 165 |
| TERIC N15 | 40 |

| Component | Proportion (g/dm³) |
|---|---|
| APS derivative (as 40% solution in SOLVESSO 150) | 69* |
| SOLVESSO 150 | made up to 1 liter |

*69 g added dissolved in SOLVESSO 150 to 40% w/w

An pesticide formulation concentrate of the above composition was formed by dissolving the lambda-cyhalothrin in 90% of the SOLVESSO 150. To this solution was added the TERIC N15 and APS derivative and the composition made up to 1 liter in volume by adding the remaining SOLVESSO 150.

The active component, lambda-cyhalothrin is a synthetic pyrethroid. The resultant pesticide formulation is of relatively low active ingredient loading. The APS derivative used in the formulation was the product of a $C_{12}$-alkylsuccinic anhydride derivative reacted with n-butylglucoside (that is a $C_4$-APS reacted with a $C_{12}$ chain ASA).

The pesticide formulation was quite stable and after 1 ml was diluted in 100 mls of soft 1 WHO and 3 WHO water, <0.1 ml of cream was observed as remaining after 30 minutes. (The World Health Organisation defines 1 WHO water as comprising 342 ppm calcium ions and 3 WHO water as comprising 1026 ppm calcium ions.)

EXAMPLE 28

| Component | Proportion (g/dm³) |
|---|---|
| Permethrin 99% w/w, Technical Grade | 505 |
| TERIC 200 | 20 |
| Atlas G1285 | 20 |
| APS derivative (as 40% solution in SOLVESSO 150) | 60 |
| SOLVESSO 150 | Made up to 1 liter |

A pesticide formulation concentrate of the above composition was formed by dissolving the permethrin in 90% of the SOLVESSO 150. To this solution was added the TERIC 200 and Atlas G1285 (a castor oil ethoxylate) and APS derivative and the composition made up to 1 liter in volume by adding the remaining SOLVESSO 150.

The resultant pesticide formulation is of relatively high active ingredient loading. The APS derivative used in the formulation was the product of a $C_{12}$-alkenylsuccinic anhydride derivative reacted with n-butylglucoside (that is a $C_4$-APS reacted with a $C_{12}$ chain ASA).

The pesticide formulation was quite stable and exhibited <0.1 ml of cream after 30 minutes in soft 1 WHO and 3 WHO water.

EXAMPLE 29

| Component | Proportion (g/dm³) |
|---|---|
| trifluralin 99.5% w/w, Technical Grade | 402 |
| TERIC 200 | 32.5 |
| TERIC GN8 | 17.5 |
| APS derivative (as 40% solution in SOLVESSO 150) | 50 |
| SOLVESSO 150 | Made up to 1 liter |

A herbicide formulation of the above composition was formed by dissolving the trifluralin in 90% of the SOLVESSO 150. To this solution was added the TERIC 200 and TERIC GN8 and APS derivative and the composition made up to 1 liter in volume by adding the remaining SOLVESSO 150.

The resultant herbicide is of relatively high active ingredient loading. The APS derivative used in the formulation was the product of a $C_{10}$-alkenylsuccinic anhydride derivative reacted with n-butylglucoside (that is a $C_4$-APS reacted with a $C_{10}$ chain ASA). The herbicide formulation was quite stable.

EXAMPLE 30

| Component | Proportion (g/dm³) |
|---|---|
| lambda-cyhalothrin 85% w/w, Technical Grade | 59 |
| TERIC N15 | 28 |
| APS derivative as 40% solution in SOLVESSO 150 | 42 |
| SOLVESSO 150 | Made up to 1 liter |

A pesticide formulation concentrate of the above composition was formed by dissolving the lambda-cyhalothrin in 90% of the SOLVESSO 150. To this solution was added the TERIC N15 and APS derivative and the composition made up to 1 liter in volume by adding the remaining SOLVESSO 150.

The resultant pesticide formulation is of relatively low active ingredient loading that is, 50 g/dm³ lambda-cyhalothrin. The APS derivative used in the formulation was the product of a $C_{12}$-alkenylsuccinic anhydride derivative reacted with n-butylglucoside (that is a $C_4$-APS reacted with a $C_{12}$ chain ASA).

The pesticide formulation was quite stable after 1 ml was diluted in 100 mls of soft 1 WHO and 3 WHO water. The formulation met standard requirements of less than 0.1 ml of cream observed remaining after 30 minutes.

EXAMPLE 31

| Component | Proportion (g/dm³) |
|---|---|
| alpha-CYPERMETHRIN (Technical Grade) | 12.3 |
| SOLVESSO 200 | 24 |
| TERIC 200 | 48 |
| APS derivative as 50% solution in SOLVESSO 200 | 16 |
| TWEEN 85 | 16 |
| water | 870 |

A micro-emulsion formulation suitable for animal health applications was formed by heating together at 70° C. the technical grade alpha-cypermethrin (a synthetic pyrethroid), SOLVESSO 200, TERIC 200, APS derivative and TWEEN 85. The water, also at 70° C. was added gradually and the micro-emulsion so formed was allowed to cool. The micro-emulsion was clear below 50° C. and stable down to 2° C.

The APS derivative used in the formulation was the product of a $C_{12}$-alkenylsuccinic anhydride derivative reacted with n-butylglucoside (that is a $C_4$-APS reacted with a $C_{12}$ chain ASA).

EXAMPLE 32

| Component | Proportion (g/dm³) |
|---|---|
| Lambda cyhalothrin 85% w/w, Technical Grade | 59 |
| TERIC N15 | 50 |
| APS derivative $C_6$ APS-$C_{12}$ ASA* (as 50% solution in SOLVESSO 150) | 50 |
| SOLVESSO 150 | Make up volume to 1 liter |

*Alkyl polysaccharide product derived from a $C_6$ alkyl polysaccharide and a $C_{12}$ alkenyl succinic anhydride.

An insecticide formulation concentrate of the above composition was formed by the general method disclosed in Example 30, that is by dissolving the lambda cyhalothrin in some SOLVESSO 150, then adding the TERIC N15 and APS derivative. The composition was then made up to 1 liter in volume by adding more SOLVESSO 150.

The insecticide formulation was quite stable and exhibited <0.2% of cream after 3 hours and less than 1% cream after 24 hours following 1% v/v dilution in soft 1 WHO and 3 WHO water at 20° and 30° C.

EXAMPLE 33

| Component | Proportion (g/dm³) |
|---|---|
| Lambda cyhalothrin 85% w/w, Technical Grade | 59 |
| TERIC N15 | 50 |
| APS derivative $C_6$ APS-$C_{12}$ ASA (as 50% SOLVESSO 150 solution) | 50 |
| SOLVESSO 150 | Make up volume to 1 liter |

A pesticide formulation concentrate of the above composition was formed by the general method disclosed in Example 30, that is by dissolving the lambda cyhalothrin in some SOLVESSO 150, then adding the TERIC N15 and APS derivative. The composition was then made up to 1 liter in volume by adding more SOLVESSO 150.

The pesticide formulation was quite stable and exhibited <0.2% of cream after 3 hours and less than 1% cream after 24 hours following 1% v/v dilution in soft, 1 WHO and 3 WHO water at 20° and 30° C.

EXAMPLE 34

| Component | Proportion (g/dm³) |
|---|---|
| Lambda cyhalothrin 85% w/w, Technical Grade | 59 |
| 12-15A15* | |
| APS derivative $C_6$ APS-$C_8$ ASA (as 50% SOLVESSO 150 solution) | 60 |
| SOLVESSO 150 | Make up volume to 1 liter |

**12-15A15 is a $C_{12}$–$C_{15}$ alcohol exthoxylated with 15 moles of ethylene oxide.

A pesticide formulation concentrate of the above composition was formed by the general method disclosed in Example 30, that is by dissolving the lambda cyhalothrin in some SOLVESSO 150, then adding the 12-15A15 and APS derivative. The composition was then made up to 1 liter in volume by adding more SOLVESSO 150.

The pesticide formulation was quite stable and exhibited <0.2% of cream after 3 hours and less than 1% cream after 24 hours following 1% v/v dilution in soft 1 WHO and 3 WHO water at 20° and 30° C.

EXAMPLE 35

| Component | Proportion (g/dm³) |
|---|---|
| Lambda cyhalothrin 85% w/w, Technical Grade | 59 |
| 12-15A15 | 50 |
| APS derivative $C_{10}$ APS-$C_8$ ASA (as 50% SOLVESSO 150 solution) | 50 |
| SOLVESSO 150 | to make up volume to 1 liter |

A pesticide formulation concentrate of the above composition was formed by the general method disclosed in Example 30, that is by dissolving the lambda cyhalothrin in some SOLVESSO 150, then adding the 12-15A15 and APS derivative. The composition was then made up to 1 liter in volume by adding more SOLVESSO 150.

The pesticide formulation was quite stable and exhibited <0.2% of cream after 3 hours and less than 1% cream after 24 hours following 1% v/v dilution in soft, 1 WHO and 3 WHO water at 20° and 30° C.

EXAMPLE 36

| Component | Proportion (g/dm³) |
|---|---|
| Lambda cyhalothrin 85% w/w, Technical Grade | 59 |
| 12-15A15 | 40 |
| APS derivative $C_8$ APS-$C_8$ ASA (as 50% SOLVESSO 150 solution) | 60 |
| SOLVESSO 150 | Make up volume to 1 liter |

A pesticide formulation concentrate of the above composition was formed by the general method disclosed in Example 30, that is by dissolving the lambda cyhalothrin in some SOLVESSO 150, then adding the 12-15A15 and APS derivative. The composition was then made up to 1 liter in volume by adding more SOLVESSO 150.

The pesticide formulation was quite stable and exhibited <0.2% of cream after 3 hours and less than 1% cream after 24 hours following 1% v/v dilution in soft, 1 WHO and 3 WHO water at 20° and 30° C.

EXAMPLE 37

| Component | Proportion (g/dm³) |
|---|---|
| Lambda cyhalothrin 85% w/w, Technical Grade | 59 |
| 12-15A15 | 30 |
| APS derivative $C_6$ APS-$C_{12}$ ASA (as 50% SOLVESSO 150 solution) | 70 |
| SOLVESSO 150 | Make up volume to 1 liter |

A pesticide formulation concentrate of the above composition was formed by the general method disclosed in Example 30, that is by dissolving the lambda cyhalothrin in some SOLVESSO 150, then adding the 12-15A15 and APS derivative. The composition was then made up to 1 liter in volume by adding more SOLVESSO 150.

The pesticide formulation was quite stable and exhibited <0.2% of cream after 3 hours and less than 1% cream after 24 hours following 1% v/v dilution in soft, 1 WHO and 3 WHO water at 20° and 30° C.

EXAMPLE 38

| Component | Proportion (g/dm$^3$) |
|---|---|
| Trifluralin | 416.7 |
| 96% w/w, Technical Grade | |
| TERIC 200 | 50 |
| APS derivative $C_6$ APS-$C_{10}$ ASA | 50 |
| (as 50% SOLVESSO 150 solution) | |
| SOLVESSO 150 | Make up volume to 1 liter |

A pesticide formulation concentrate of the above composition was formed by the general method disclosed in Example 30, that is by dissolving the trifluralin in some SOLVESSO 150, then adding the TERIC 200 and APS derivative. The composition was then made up to 1 liter in volume by adding more SOLVESSO 150.

The pesticide formulation was quite stable and exhibited <0.2% of cream after 3 hours and less than 1% cream after 24 hours following 1% v/v dilution in soft, 1 WHO and 3 WHO water at 20° and 30° C.

EXAMPLE 39

| Component | Proportion (g/dm$^3$) |
|---|---|
| Trifluralin | 500 |
| 96% w/w, Technical Grade | |
| TERIC 200 | 27.5 |
| TERIC GN8 | 22.5 |
| APS derivative $C_6$ APS-$C_{10}$ ASA | 50 |
| (as 50% SOLVESSO 150 solution) | |
| SOLVESSO 150 | Make up volume to 1 liter |

A pesticide formulation concentrate of the above composition was formed by the general method disclosed in Example 30, that is by dissolving the trifluralin in some SOLVESSO 150, then adding the TERIC and APS derivative. The composition was then made up to 1 liter in volume by adding more SOLVESSO 150.

The pesticide formulation was quite stable and exhibited <0.2% of cream after 3 hours and less than 1% cream after 24 hours following 1% v/v dilution in soft, 1 WHO and 3 WHO water at 20° and 30° C.

EXAMPLE 40

| Component | Proportion (g/dm$^3$) |
|---|---|
| Chlorpyrifos | 521 |
| 96% w/w, Technical Grade | |
| ATLAS G1284* | 45 |
| APS derivative C8 APS-C8 ASA | 55 |
| (as 50% SOLVESSO 150 solution) | |
| SOLVESSO 150 | Make up volume to 1 liter |

*ATLAS G1284 is a castor oil ethoxylate.

A pesticide formulation concentrate of the above composition was formed by the general method disclosed in Example 30, that is by dissolving the chlorpyrifos in some SOLVESSO 150, then adding the ATLAS G1284 and APS derivative. The composition was then made up to 1 liter in volume by adding more SOLVESSO 150.

The pesticide formulation was quite stable and exhibited <0.2% of cream after 3 hours and less than 1% cream after 24 hours following 1% v/v dilution in soft, 1 WHO and 3 WHO water at 20° and 30° C.

EXAMPLE 41

| Component | Proportion (g/dm$^3$) |
|---|---|
| Chlorpyrifos | 521 |
| 96% w/w, Technical Grade | |
| ATLAS G1284* | 45 |
| APS derivative $C_{8/10}$ | 55 |
| (ALFOL 810 $C_8$ ASA | |
| (as 50% SOLVESSO 150 solution) | |
| SOLVESSO 150 | Make up volume to 1 liter |

*ATLAS G1284 is a castor oil ethoxylate.

A pesticide formulation concentrate of the above composition was formed by the general method disclosed in Example 30, that is by dissolving the chlorpyrifos in some SOLVESSO 150, then adding the ATLAS G1284 and APS derivative. The composition was then made up to 1 liter in volume by adding more SOLVESSO 150.

The pesticide formulation was quite stable and exhibited <0.2% of cream after 3 hours and less than 1% cream after 24 hours following 1% v/v dilution in soft, 1 WHO and 3 WHO water at 20° and 30° C.

EXAMPLE 42

| Component | Proportion (g/dm$^3$) |
|---|---|
| FUSILADE | 275 |
| 90.9% w/w, Technical Grade | |
| TERIC GN8 | 40 |
| TERIC 200 | 4 |
| APS derivative $C_{8/10}$ | 36 |
| (ALFOL 810D-$C_8$ ASA | |
| (as 50% SOLVESSO 150 solution) | |
| SOLVESSO 150 | Make up volume to 1 liter |

A herbicide formulation concentrate of the above composition was formed by the general method disclosed in Example 30, that is by dissolving the FUSILADE in some SOLVESSO 150, then adding the TERICs and APS derivative. The herbicide composition was then made up to 1 liter in volume by adding more SOLVESSO 150.

The herbicide formulation was quite stable and exhibited <0.2% of cream after 3 hours and less than 1% cream after 24 hours following 1% v/v dilution in soft, 1 WHO and 3 WHO water at 20° and 30° C.

EXAMPLE 43

| Component | Proportion (g/dm$^3$) |
|---|---|
| FUSILADE | 275 |
| 90.9% w/w, Technical Grade | |
| TERIC GN8 | 24 |
| TERIC 200 | 16 |

17

-continued

| Component | Proportion (g/dm³) |
|---|---|
| APS derivative C$_{8/10}$ (ALFOL 810D-C$_8$ ASA (as 50% SOLVESSO 150 solution) | 40 |
| SOLVESSO 150 | Make up volume to 1 liter |

A herbicide formulation concentrate of the above composition was formed by the general method disclosed in Example 30, that is by dissolving the FUSILADE in some SOLVESSO 150, then adding the TERICs and APS derivative. The composition was then made up to 1 liter in volume by adding more SOLVESSO 150.

The herbicide formulation was quite stable and exhibited <0.2% of cream after 3 hours and less than 1% cream after 24 hours following 1% v/v dilution in soft, 1 WHO and 3 WHO water at 20° and 30° C.

EXAMPLE 44

| Component | Proportion (g/dm³) |
|---|---|
| FUSILADE 90.9% w/w, Technical Grade | 275 |
| TERIC N15 | 16 |
| ATLAS G1284 | 24 |
| APS derivative C$_{8/10}$ (ALFOL 810D-C$_8$ ASA (as 50% SOLVESSO 150 solution) | 20 |
| SOLVESSO 150 | Make up volume to 1 liter |

*ATLAS G1284 is a castor oil ethoxylate.

A herbicide formulation concentrate of the above composition was formed by the general method disclosed in Example 30, that is by dissolving the FUSILADE in some SOLVESSO 150, then adding the TERIC, ATLAS and APS derivative. The composition was then made up to 1 liter in volume by adding more SOLVESSO 150.

The herbicide formulation was quite stable and exhibited <0.2% of cream after 3 hours and less than 1% cream after 24 hours following 1% v/v dilution in soft, 1 WHO and 3 WHO water at 20° and 30° C.

EXAMPLE 45

| Component | Proportion (g/dm³) |
|---|---|
| 2,4-D butyl ester 96% w/w, Technical Grade | 750 |
| TERIC 200 | 28 |
| APS derivative C8APS-C8ASA (as 50% SOLVESSO 150 solution) | 52 |
| SOLVESSO 150 | to make up volume to 1 liter |

A herbicide formulation concentrate of the above composition was formed by the general method disclosed in Example 30, that is by dissolving the 2,4-D butylester in some SOLVESSO 150, then adding the TERIC and APS derivative. The composition was then made up to 1 liter in volume by adding more SOLVESSO 150.

The herbicide formulation was quite stable and exhibited <0.2% of cream after 3 hours and less than 1% cream after 24 hours following 1% v/v dilution in soft, 1 WHO and 3 WHO water at 20° and 30° C.

18

EXAMPLE 46

| Component | Proportion (g/dm³) |
|---|---|
| Glyphosate-IPA salt (as 60% solution in water) | 485 |
| C$_6$APS-C$_8$ASA triethanolamine salt (as 40% solution in water) | 52 |
| C8/10 APS (ATPLUS 3001A) (as 70% solution in water) | 59 |
| Water | Make up to 1 liter |

A herbicide formulation concentrate of the above composition was formed by the general method disclosed in Example 30, that is by adding the glyphosate-IPA salt to some water, then adding the ATPLUS and C$_6$APS-C$_8$ASA triethanolamine salt derivative. The composition was then made up to 1 liter in volume by adding more water.

The herbicide formulation was quite stable.

It will be readily apparent to the person skilled in the art that the alkyl polysaccharide derivatives of the present invention may also be suitable for use in formulas and other products requiring a surfactant component.

EXAMPLE 47

COLORADO BEETLE (LEPTINOTARSA DECEMLINETA) ON POTATO LEAVES.

L decemlineta beetle eggs were collected from a laboratory strain of the beetle and maintained at 23° C. and a photoperiod of 16/8 [L:D]. After hatching the larvae were reared on potato leaves and used for testing immediately after moulting to the second instar.

Fresh potato leaves were dipped in appropriate dilutions (in tap water) of the selected adjuvants and/or carbaryl (1-naphthyl methylcarbamate) as the insecticide, air dried and offered to the larvae.

Blank runs were carried out using water alone and adjuvant alone (1% aqueous solution). These blank runs indicated that neither water alone nor the solution of the adjuvant acted as an insecticide.

Insecticidal activity tests were carried out using the following treatments:

(i) insecticide solution in water (at a concentration of 4 mg/l active insecticide—the LC50 of the insecticide estimated from preliminary testing); for comparison and (ii) solution of insecticide (4 mg/l active insecticide) and adjuvant (0.1% concentration).

Each experiment was carried out in at least three replicates using 10 larvae each. The percentage of larvae killed after 24 hours by each treatment was noted. An Abbott correction was calculated for the mortality data and tha data rescaled so that treatment with insecticide alone was assessed as having 50% mortality. From the resulting data the Adjuvancy Effectiveness Ratio (AER) was calculated as:

AER=(% mortality using insecticide and adjuvant)/(% mortality using insecticide alone)

Table 1 below sets out the results obtained.

TABLE 1

| Run No | Adjuvant | Mortality | AER |
|---|---|---|---|
| 1 | none | 50 | 1* |
| 2 | C$_4$APS-C$_{12}$ASA | 100 | 2** |

TABLE 1-continued

| Run No | Adjuvant | Mortality | AER |
|---|---|---|---|
| 3 | $C_4APS\text{-}C_8ASA$ | 82.3 | 1.65 |

*by definition this figure is 1
**minimum figure - limited by the upper sensitivity of the test.

The results in Table 1 clearly show the improvement in mortality which is achieved by using insecticide and adjuvant as compared with using insecticide alone.

EXAMPLE 48
EGYPTIAN COTTON LEAFWORM (SPODOPTERA LITTORALIS) ON CASTOR BEAN LEAVES.

S littoralis eggs were collected from a laboratory rearing maintained at 23° C. and a photoperiod of 16/8 [L:D]. After hatching the larvae were reared on an artificial diet and used for testing immediately after moulting to the third instar.

Fresh castor bean leaves were dipped in appropriate dilutions (in tap water) of the selected adjuvant and/or deltamethrin [(S)-alpha-cyano-3-phenoxybenzyl (1R3R)-3-(2,2-dibromovinyl)-2,2-dimethyl-cyclopropanecarboxylate] as the insecticide, air dried and offered to the larvae.

Blank runs were carried out using water alone and adjuvant alone (1% aqueous solution), these blank runs indicated that neither water alone nor the solution of the adjuvant acted as an insecticide.

Insecticidal activity tests were carried out using the following treatments:

(i) insecticidal solution in water (at a concentration of 1 mg/l active insecticide—the LC50 of the insecticide estimated from preliminary testing); for comparison and (ii) solution of insecticide (1 mg/l active insecticide) and adjuvant (0.1% concentration).

Each experiment was carried out in at least three replicates using 10 larvae each. the percentage of larvae killed after 24 hours by each treatment was noted and the data treated statistically as described in Adjuvancy Example 47. The results are set out in Table 2 below:

TABLE 2

| Run No | Adjuvant | Mortality | AER |
|---|---|---|---|
| 1 | none | 50 | 1* |
| 3 | $C_4APS\text{-}C_8ASA$ | 77.4 | 1.54 |

*by definition this figure is 1

The results in Table 2 clearly show the improvement in mortality achieved by using an insecticide and adjuvant as compared with insecticide alone.

While the invention has been explained in relation to its preferred embodiments it is to be understood that various modifications thereof will become apparent to those skilled in the art upon reading the specification. Therefore, it is to be understood that the invention disclosed herein is intended cover such modifications as fall within the scope of the appended claims.

We claim:

1. A composition comprising the product of a reaction between an alkenyl succinic anhydride and at least one alkyl polysaccharide.

2. An alkyl polysaccharide derivative of the formula I, $$R^1-(OG)_n(X)_m \quad (I)$$

where
$R^1$ is hydrogen or a hydrophobic moiety;
G is a saccharide residue;
X is an alkenyl or alkyl succinic anhydride residue; and
n and m are independently chosen from an average value which is between 1 and 200 or a salt of thereof.

3. An alkylpolysaccharide derivative according to claim 2 wherein;
$R^1$ is a hydrophobic moiety and comprises a substituted hydrocarbyl group;
G is a saccharide residue comprising fructose, glucose, aldose, altose, idose, arabinose, xylose, lipose, ribose or mixtures thereof;
X is a succinic anhydride residue comprising a $C_1$ to $C_{40}$ linear or branched alkenyl or alkyl group; and
n is between 1 and 5.

4. An alkylpolysaccharide derivative according to claim 3 wherein;
$R^1$ is chosen from the group comprising $C_1$ to $C_{40}$ branched or linear alkyl or alkenyl groups;
G is a glucose residue;
X is a succinic anhydride residue comprising a $C_6$ to $C_{30}$ linear alkyl or alkenyl group; and
n is between 1 and 3.

5. An alkyl polysaccharide derivative according to claim 4 wherein in the succinic anhydride residue the alkenyl or alkyl group is chosen from the group comprising $C_8$ to $C_{30}$ linear alkenyl or alkyl groups.

6. An alkyl polysaccharide derivative according to claim 4 wherein in the succinic anhydride residue the alkenyl group is chosen from the group comprising $C_8$ to $C_{30}$ linear alkenyl groups.

7. An alkyl polysaccharide derivative according to claim 6 wherein in the succinic anhydride residue the alkenyl or alkyl chain is chosen from the group comprising $C_8$, $C_{10}$, $C_{12}$, $C_{14}$, $C_{16}$ or $C_{18}$.

8. An alkyl polysaccharide derivative according to claim 7 wherein $R^1$ is chosen from the group comprising $C_1$ to $C_{14}$ branched or linear alkyl groups.

9. An alkyl polysaccharide derivative according to claim 8 wherein $R^1$ is chosen from the group comprising $C_4$ to $C_{12}$ linear alkyl groups.

10. An alkylpolysaccharide derivative of formula II;

wherein
$R^1$ and $R^2$ are independently hydrogen or $C_1$ to $C_{40}$ branched or linear alkyl groups,
$R^3$ and $R^4$ are independently chosen from the group comprising hydrogen, hydroxy, alkyl or alkoxy groups, and
n is 1 to 100 or a salt of thereof.

11. An alkyl polysaccharide derivative according to claim 10 wherein
$R^1$ is chosen from the group comprising hydrogen and $C_1$ to $C_{12}$ branched or linear alkyl groups;
$R^2$ is chosen from the group comprising $C_3$ to $C_{27}$ linear alkyl groups;

$R^3$ and $R^4$ are hydroxy;
and n is between 1 and 2.5.

12. An alkylpolysaccharide derivatives of formula III;

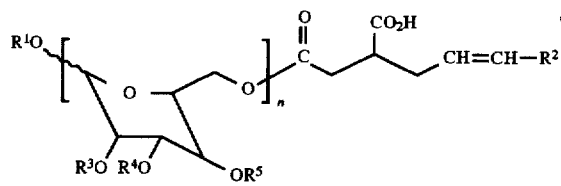

where $R^1$ is chosen from $C_1$ to $C_{12}$ branched or linear alkyl groups, $R^2$ is chosen from $C_3$ to $C_{27}$ branched or linear alkyl groups, $R^3$, $R^4$ and $R^5$ are independently chosen from the group comprising hydrogen, alkyl or acyl groups, and n is 1 to 100 or a salt of thereof.

13. A method of preparation of alkylpolysaccharide derivatives as defined according to claim 2 inclusive comprising reacting at least one alkenyl or alkyl succinic anhydride with at least one alkyl polysaccharide.

14. A method of preparation of alkyl polysaccharide derivatives as defined according to claim 10 comprising reacting an alkenyl succinic anhydride with at least one alkyl polysaccharide.

15. A method of preparation according to claim 14 wherein the alkylpolysaccharide is reacted with the alkenyl or alkyl succinic anhydride in the presence of at least one alcohol.

16. A method of preparation according to claim 14 wherein no solvent is used.

17. A method of preparation according to claim 13 wherein the reaction temperature is above 120° C.

18. A composition comprising the alkylpolysaccharide derivative of claim 2 wherein said composition is in the form of a macro-emulsion, micro-emulsion, emulsifiable concentrate, colloid, solution, powder or granules.

19. An agrochemical formulation, personal care product, fabric conditioner, defoamer or the like comprising the alkylpolysaccharide derivative of claim 2.

20. A pesticide or plant growth regulator composition comprising an alkylpolysaccharide derivative of claim 2, comprising an active pesticide component, solvent and surfactant.

21. A polish or textile treatment formulation comprising the alkyl polysaccharide derivative of claim 2.

22. A composition comprising the alkyl polysaccharide derivative of claim 2 wherein the alkyl polysaccharide acts as an emulsifier and/or an adjuvant.

23. A pesticide or plant growth regulator composition according to claim 20 wherein the composition is a solution, macroemulsion or microemulsion.

24. A pesticide composition according to claim 20 suitable as an insecticide agent wherein the active insecticidal component is chosen from the group comprising natural pyrethroids, synthetic pyrethroids, carbamate, organophosphates and mixtures thereof.

25. A pesticide composition according to claim 20 suitable as a herbicidal agent wherein the active herbicidal component is chosen from the group comprising phenoxypropionates, glyphosate, glyphosate salts, triketones, alkylketones, sulphonylureas and sulphonanilides.

26. A pesticide composition according to claim 25 which further comprise one or more secondary surfactants.

27. A pesticide composition according to claim 25 wherein the alkylpolysaccharide derivative acts as an adjuvant.

28. An alkali metal, alkaline earth metal or amine salt of an alkyl polysaccharide derivative according to claim 2.

* * * * *